United States Patent
Patel et al.

(10) Patent No.: US 10,953,204 B2
(45) Date of Patent: Mar. 23, 2021

(54) GUIDEWIRE WITH TACTILE FEEL

(71) Applicant: BOSTON SCIENTIFIC SCIMED, INC., Maple Grove, MN (US)

(72) Inventors: Mayur Kiran Patel, Framingham, MA (US); Gene T. Storbeck, Franklin, MA (US); Sacha Tang, Wilmington, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/864,557

(22) Filed: Jan. 8, 2018

(65) Prior Publication Data

US 2018/0193606 A1 Jul. 12, 2018

Related U.S. Application Data

(60) Provisional application No. 62/443,882, filed on Jan. 9, 2017.

(51) Int. Cl.
| | | |
|---|---|---|
| *A61M 25/09* | (2006.01) | |
| *A61L 31/02* | (2006.01) | |
| *A61L 31/04* | (2006.01) | |
| *A61L 31/06* | (2006.01) | |
| *B29L 31/00* | (2006.01) | |

(Continued)

(52) U.S. Cl.
CPC .......... *A61M 25/09* (2013.01); *A61L 31/022* (2013.01); *A61L 31/048* (2013.01); *A61L 31/06* (2013.01); *A61B 17/8897* (2013.01); *A61M 2025/09091* (2013.01); *A61M 2025/09108* (2013.01); *A61M 2025/09116* (2013.01); *A61M 2025/09133* (2013.01); *A61M 2025/09166* (2013.01); *A61M 2025/09175* (2013.01);

(Continued)

(58) Field of Classification Search
CPC combination set(s) only.
See application file for complete search history.

(56) References Cited

U.S. PATENT DOCUMENTS

| 2,824,582 A | 2/1958 | Reitherman |
| 3,467,785 A | 9/1969 | Ulrich |

(Continued)

FOREIGN PATENT DOCUMENTS

| WO | 2007047819 A1 | 4/2007 |
| WO | 2010030863 A1 | 3/2010 |

OTHER PUBLICATIONS

International Search Report and Written Opinion dated Apr. 25, 2018, for International Application No. PCT/US2018/012799 (12 pgs).

*Primary Examiner* — Sean P Dougherty
(74) *Attorney, Agent, or Firm* — Seager, Tufte & Wickhem, LLP

(57) ABSTRACT

Medical devices and methods for making and using medical devices are disclosed. An example medical device may include a guidewire. The guidewire may include a core wire having a body region and a distal tip region. A distal tip member may be disposed along the distal tip region. The distal tip member may have a proximal end. A sleeve may be disposed along the body region. The sleeve may be disposed adjacent to the proximal end of the distal tip member and extending proximally therefrom. The sleeve may include a first member and a heat shrink member. The first member may have an uneven outer surface.

13 Claims, 9 Drawing Sheets

(51) Int. Cl.
*B29C 61/02* (2006.01)
*A61B 17/88* (2006.01)

(52) U.S. Cl.
CPC . *A61M 2205/582* (2013.01); *A61M 2205/583* (2013.01); *B29C 61/02* (2013.01); *B29L 2031/7542* (2013.01)

(56) References Cited

U.S. PATENT DOCUMENTS

| | | | |
|---|---|---|---|
| 3,730,185 A | 5/1973 | Cook et al. | |
| 3,811,446 A | 5/1974 | Lerwick et al. | |
| 3,826,637 A | 7/1974 | Lecourt | |
| 3,827,225 A | 8/1974 | Schoerner | |
| 3,927,456 A | 12/1975 | Dammar | |
| 4,080,706 A | 3/1978 | Heilman et al. | |
| 4,616,788 A | 10/1986 | Finegold | |
| 4,634,042 A | 1/1987 | Smith | |
| 4,646,719 A | 3/1987 | Neuman et al. | |
| 4,654,024 A | 3/1987 | Crittenden et al. | |
| 4,676,249 A | 6/1987 | Arenas et al. | |
| 4,808,164 A | 2/1989 | Hess | |
| 4,830,460 A | 5/1989 | Goldenberg | |
| 4,832,023 A | 5/1989 | Murphy-Chutorian et al. | |
| 4,844,062 A | 7/1989 | Wells | |
| 4,850,351 A | 7/1989 | Herman et al. | |
| 4,867,173 A | 9/1989 | Leoni | |
| 4,883,458 A | 11/1989 | Shiber | |
| 4,886,490 A | 12/1989 | Shiber | |
| 4,894,051 A | 1/1990 | Shiber | |
| 4,905,698 A | 3/1990 | Strohl, Jr. et al. | |
| 4,917,085 A | 4/1990 | Smith | |
| 4,927,413 A | 5/1990 | Hess | |
| 4,979,939 A | 12/1990 | Shiber | |
| 4,984,581 A | 1/1991 | Stice | |
| 4,991,578 A | 2/1991 | Cohen | |
| 4,995,878 A | 2/1991 | Rai | |
| 5,001,825 A | 3/1991 | Halpern | |
| 5,007,896 A | 4/1991 | Shiber | |
| 5,009,655 A | 4/1991 | Daignault, Jr. et al. | |
| 5,024,651 A | 6/1991 | Shiber | |
| 5,067,489 A | 11/1991 | Lind | |
| 5,088,979 A | 2/1992 | Filipi et al. | |
| 5,108,419 A | 4/1992 | Reger et al. | |
| 5,114,399 A | 5/1992 | Kovalcheck | |
| 5,115,814 A | 5/1992 | Griffith et al. | |
| 5,122,136 A | 6/1992 | Guglielmi et al. | |
| 5,135,531 A | 8/1992 | Shiber | |
| 5,139,032 A | 8/1992 | Jahrmarkt et al. | |
| 5,147,317 A | 9/1992 | Shank et al. | |
| 5,160,342 A | 11/1992 | Reger et al. | |
| 5,187,664 A | 2/1993 | Yardley et al. | |
| 5,190,528 A | 3/1993 | Fonger et al. | |
| 5,217,026 A | 6/1993 | Stoy et al. | |
| 5,243,988 A | 9/1993 | Sieben et al. | |
| 5,246,009 A | 9/1993 | Adams | |
| 5,267,341 A | 11/1993 | Shearin | |
| 5,269,759 A | 12/1993 | Hernandez et al. | |
| 5,281,205 A | 1/1994 | McPherson | |
| 5,287,858 A | 2/1994 | Hammerslag et al. | |
| 5,290,241 A | 3/1994 | Kraus et al. | |
| 5,299,580 A | 4/1994 | Atkinson et al. | |
| 5,306,244 A | 4/1994 | Shiber | |
| 5,308,356 A | 5/1994 | Blackshear, Jr. et al. | |
| 5,338,301 A | 8/1994 | Diaz | |
| 5,353,798 A | 10/1994 | Sieben | |
| 5,364,376 A | 11/1994 | Horzewski et al. | |
| 5,366,473 A | 11/1994 | Winston et al. | |
| 5,372,144 A | 12/1994 | Mortier et al. | |
| 5,372,603 A | 12/1994 | Acker et al. | |
| 5,373,619 A | 12/1994 | Fleischhacker et al. | |
| 5,375,596 A | 12/1994 | Twiss et al. | |
| 5,379,779 A | 1/1995 | Rowland et al. | |
| 5,386,828 A | 2/1995 | Owens et al. | |
| 5,395,334 A | 3/1995 | Keith et al. | |
| 5,402,799 A | 4/1995 | Colon et al. | |
| 5,410,797 A | 5/1995 | Steinke et al. | |
| 5,421,338 A | 6/1995 | Crowley et al. | |
| 5,425,709 A | 6/1995 | Gambale | |
| 5,437,288 A * | 8/1995 | Schwartz | A61M 25/09 600/434 |
| 5,443,457 A | 8/1995 | Ginn et al. | |
| 5,449,362 A | 9/1995 | Chaisson et al. | |
| 5,450,853 A | 9/1995 | Hastings et al. | |
| 5,460,185 A | 10/1995 | Johnson et al. | |
| 5,465,733 A | 11/1995 | Hinohara et al. | |
| 5,466,234 A | 11/1995 | Loeb et al. | |
| 5,484,444 A | 1/1996 | Braunschweiler et al. | |
| 5,488,959 A | 2/1996 | Ales | |
| 5,493,770 A | 2/1996 | Anichini et al. | |
| 5,507,995 A * | 4/1996 | Schweich, Jr. | A61M 25/0013 264/293 |
| 5,517,989 A | 5/1996 | Frisbie et al. | |
| 5,520,189 A | 5/1996 | Malinowski et al. | |
| 5,540,680 A | 7/1996 | Guglielmi et al. | |
| 5,542,434 A | 8/1996 | Imran et al. | |
| 5,546,958 A | 8/1996 | Thorud et al. | |
| 5,551,443 A | 9/1996 | Sepetka et al. | |
| 5,554,114 A | 9/1996 | Wallace et al. | |
| 5,554,139 A | 9/1996 | Okajima | |
| 5,556,382 A | 9/1996 | Adams | |
| 5,562,669 A | 10/1996 | McGuire | |
| 5,573,520 A * | 11/1996 | Schwartz | A61M 25/0013 604/264 |
| 5,573,531 A | 11/1996 | Gregory | |
| 5,579,707 A | 12/1996 | Erwin | |
| 5,588,442 A | 12/1996 | Scovil et al. | |
| 5,588,443 A | 12/1996 | Davidson | |
| 5,599,492 A | 2/1997 | Engelson | |
| 5,603,694 A | 2/1997 | Brown et al. | |
| 5,605,162 A | 2/1997 | Mirzaee et al. | |
| 5,606,979 A | 3/1997 | Hodgson | |
| 5,622,184 A | 4/1997 | Ashby et al. | |
| 5,630,839 A | 5/1997 | Corbett, III et al. | |
| 5,643,297 A | 7/1997 | Nordgren et al. | |
| 5,660,180 A | 8/1997 | Malinowski et al. | |
| 5,678,296 A | 10/1997 | Fleischhacker et al. | |
| 5,683,451 A | 11/1997 | Lenker et al. | |
| 5,690,613 A | 11/1997 | Verbeek | |
| 5,695,468 A | 12/1997 | Lafontaine et al. | |
| 5,701,901 A | 12/1997 | Lum et al. | |
| 5,718,683 A | 2/1998 | Ressemann et al. | |
| 5,720,300 A | 2/1998 | Fagan et al. | |
| 5,728,122 A | 3/1998 | Leschinsky et al. | |
| 5,741,429 A * | 4/1998 | Donadio, III | A61M 25/0043 216/10 |
| 5,746,701 A * | 5/1998 | Noone | A61M 25/09 600/585 |
| 5,749,371 A | 5/1998 | Zadini et al. | |
| 5,749,848 A | 5/1998 | Jang et al. | |
| 5,750,206 A | 5/1998 | Hergenrother et al. | |
| 5,776,160 A | 7/1998 | Pasricha et al. | |
| 5,785,685 A | 7/1998 | Kugler et al. | |
| 5,797,856 A * | 8/1998 | Frisbie | A61M 25/09 600/585 |
| 5,813,997 A | 9/1998 | Imran et al. | |
| 5,824,055 A | 10/1998 | Spiridigliozzi et al. | |
| 5,830,155 A | 11/1998 | Frechette et al. | |
| 5,836,940 A | 11/1998 | Gregory | |
| 5,865,768 A | 2/1999 | Orr | |
| 5,876,783 A | 3/1999 | Dobson | |
| 5,893,852 A | 4/1999 | Morales | |
| 5,897,819 A | 4/1999 | Miyata et al. | |
| 5,908,385 A | 6/1999 | Chechelski et al. | |
| 5,910,364 A | 6/1999 | Miyata et al. | |
| 5,916,166 A | 6/1999 | Reiss et al. | |
| 5,947,404 A | 9/1999 | Dolgas et al. | |
| 5,954,671 A | 9/1999 | O'Neill | |
| 5,954,737 A | 9/1999 | Lee | |
| 5,954,741 A | 9/1999 | Fox | |
| 5,989,210 A | 11/1999 | Morris et al. | |
| 5,997,487 A | 12/1999 | Kolehmainen et al. | |
| 6,019,736 A | 2/2000 | Avellanet et al. | |
| 6,042,553 A | 3/2000 | Solar et al. | |
| 6,042,876 A | 3/2000 | Deem | |

(56) References Cited

U.S. PATENT DOCUMENTS

| | | |
|---|---|---|
| 6,048,299 A | 4/2000 | Hoffmann |
| 6,050,972 A | 4/2000 | Zadno-Azizi et al. |
| 6,053,900 A | 4/2000 | Brown et al. |
| 6,059,713 A | 5/2000 | Urick et al. |
| 6,059,738 A | 5/2000 | Stoltze et al. |
| 6,062,504 A | 5/2000 | Luciani |
| 6,071,286 A | 6/2000 | Mawad |
| 6,074,339 A | 6/2000 | Gambale et al. |
| 6,074,362 A | 6/2000 | Jang et al. |
| 6,078,831 A | 6/2000 | Belef et al. |
| 6,096,054 A | 8/2000 | Wyzgala et al. |
| 6,106,485 A * | 8/2000 | McMahon ............ A61M 25/09 600/585 |
| 6,106,515 A | 8/2000 | Winston et al. |
| 6,106,538 A | 8/2000 | Shiber |
| 6,113,557 A | 9/2000 | Fagan et al. |
| 6,120,511 A | 9/2000 | Chan |
| 6,139,557 A | 10/2000 | Passafaro et al. |
| 6,152,946 A | 11/2000 | Broome et al. |
| 6,165,140 A * | 12/2000 | Ferrera ................ A61M 25/09 600/585 |
| 6,171,250 B1 | 1/2001 | White et al. |
| 6,176,844 B1 | 1/2001 | Lee |
| 6,178,346 B1 | 1/2001 | Amundson et al. |
| 6,179,788 B1 | 1/2001 | Sullivan |
| 6,187,007 B1 | 2/2001 | Frigg et al. |
| 6,193,706 B1 | 2/2001 | Thorud et al. |
| RE37,148 E | 4/2001 | Shank |
| 6,210,312 B1 | 4/2001 | Nagy |
| 6,216,028 B1 | 4/2001 | Haynor et al. |
| 6,217,554 B1 | 4/2001 | Green |
| 6,224,570 B1 | 5/2001 | Le et al. |
| 6,238,412 B1 | 5/2001 | Dubrul et al. |
| 6,241,690 B1 | 6/2001 | Burkett et al. |
| 6,245,030 B1 | 6/2001 | DuBois et al. |
| 6,248,076 B1 | 6/2001 | White et al. |
| 6,251,107 B1 | 6/2001 | Schaer |
| 6,261,246 B1 | 7/2001 | Pantages et al. |
| 6,267,732 B1 | 7/2001 | Heneveld et al. |
| 6,296,616 B1 | 10/2001 | McMahon |
| 6,340,441 B1 | 1/2002 | Meyer et al. |
| 6,356,791 B1 | 3/2002 | Westlund et al. |
| 6,383,145 B1 | 5/2002 | Worm et al. |
| 6,387,060 B1 * | 5/2002 | Jalisi ................ A61M 25/0043 600/585 |
| 6,391,044 B1 | 5/2002 | Yadav et al. |
| 6,428,559 B1 | 8/2002 | Johnson |
| 6,445,939 B1 | 9/2002 | Swanson et al. |
| 6,461,311 B2 | 10/2002 | DuBois et al. |
| 6,464,651 B1 | 10/2002 | Hiejima et al. |
| 6,468,227 B2 | 10/2002 | Zimmon |
| 6,485,485 B1 | 11/2002 | Winston et al. |
| 6,488,655 B1 * | 12/2002 | Wantink ................ A61M 25/09 604/103.06 |
| 6,494,894 B2 | 12/2002 | Mirarchi |
| 6,512,958 B1 | 1/2003 | Swoyer et al. |
| 6,527,732 B1 | 3/2003 | Strauss et al. |
| 6,528,754 B2 | 3/2003 | Okada et al. |
| 6,529,760 B2 | 3/2003 | Pantages et al. |
| 6,558,502 B2 | 5/2003 | Divino, Jr. et al. |
| 6,579,246 B2 | 6/2003 | Jacobsen et al. |
| 6,585,654 B2 | 7/2003 | White et al. |
| 6,589,281 B2 | 7/2003 | Hyde, Jr. |
| 6,603,994 B2 | 8/2003 | Wallace et al. |
| 6,607,530 B1 | 8/2003 | Carl et al. |
| 6,615,067 B2 | 9/2003 | Hoek et al. |
| 6,641,573 B1 | 11/2003 | Parodi |
| 6,641,603 B2 | 11/2003 | Walker et al. |
| 6,656,203 B2 | 12/2003 | Roth et al. |
| 6,676,590 B1 | 1/2004 | Urick et al. |
| 6,679,893 B1 | 1/2004 | Tran |
| 6,692,446 B2 | 2/2004 | Hoek |
| 6,694,595 B1 | 2/2004 | Jalisi et al. |
| 6,699,260 B2 | 3/2004 | Dubrul et al. |
| 6,752,819 B1 | 6/2004 | Brady et al. |
| 6,761,696 B1 | 7/2004 | Wong |
| 6,763,833 B1 | 7/2004 | Khera et al. |
| 6,767,327 B1 | 7/2004 | Corl et al. |
| 6,770,035 B2 | 8/2004 | White et al. |
| 6,779,257 B2 | 8/2004 | Kiepen et al. |
| 6,783,548 B2 | 8/2004 | Hyde, Jr. |
| 6,796,945 B2 | 9/2004 | Belef et al. |
| 6,866,657 B2 | 3/2005 | Shchervinsky |
| 6,911,036 B2 | 6/2005 | Douk et al. |
| 6,994,315 B2 | 2/2006 | Ryan et al. |
| 7,018,346 B2 | 3/2006 | Griffin et al. |
| 7,022,109 B1 | 4/2006 | Ditto |
| 7,041,097 B1 | 5/2006 | Webler |
| 7,074,197 B2 | 7/2006 | Reynolds et al. |
| 7,077,812 B2 | 7/2006 | Naghavi |
| 7,094,294 B2 | 8/2006 | Shiota |
| 7,118,539 B2 | 10/2006 | Vrba et al. |
| 7,137,395 B2 | 11/2006 | Fried et al. |
| 7,150,723 B2 | 12/2006 | Meguro et al. |
| 7,157,766 B2 | 1/2007 | Gau et al. |
| 7,172,558 B2 | 2/2007 | Olson, Jr. |
| 7,189,198 B2 | 3/2007 | Harburn et al. |
| 7,241,310 B2 | 7/2007 | Taylor et al. |
| 7,283,878 B2 | 10/2007 | Brostrom et al. |
| 7,297,154 B2 | 11/2007 | Tu et al. |
| 7,335,205 B2 | 2/2008 | Aeschlimann et al. |
| 7,399,283 B2 | 7/2008 | Kato |
| 7,452,369 B2 | 11/2008 | Barry |
| 7,465,304 B1 | 12/2008 | Haufe et al. |
| 7,488,304 B2 | 2/2009 | Goodin et al. |
| RE40,796 E | 6/2009 | O'Neill |
| 7,553,287 B2 | 6/2009 | Reynolds et al. |
| 7,591,830 B2 | 9/2009 | Rutter |
| 7,650,178 B2 | 1/2010 | Scheffler |
| 7,651,578 B2 | 1/2010 | Sharrow et al. |
| 7,662,328 B2 | 2/2010 | Holzapfel et al. |
| 7,686,845 B2 | 3/2010 | Sequin et al. |
| 7,699,792 B2 | 4/2010 | Hofmann et al. |
| 7,717,864 B1 | 5/2010 | Grandfield et al. |
| 7,734,343 B2 | 6/2010 | Ransbury et al. |
| 7,753,859 B2 | 7/2010 | Kinoshita et al. |
| 7,767,219 B2 | 8/2010 | Weber et al. |
| 7,771,446 B2 | 8/2010 | Rutter |
| 7,842,012 B2 | 11/2010 | Ellis et al. |
| 7,862,577 B2 | 1/2011 | Gray et al. |
| 7,878,984 B2 | 2/2011 | Jacobsen et al. |
| 7,879,081 B2 | 2/2011 | DiMatteo et al. |
| 7,913,483 B2 | 3/2011 | Qiu et al. |
| 7,918,947 B2 | 4/2011 | Kato |
| 7,998,090 B2 | 4/2011 | Simpson et al. |
| 7,967,762 B2 | 6/2011 | Corl et al. |
| 8,002,714 B2 | 8/2011 | Bakos |
| 8,021,311 B2 | 9/2011 | Munoz et al. |
| 8,022,331 B2 | 9/2011 | Reynolds et al. |
| 8,067,073 B2 | 11/2011 | Zhong et al. |
| 8,088,121 B2 | 1/2012 | Nishide et al. |
| 8,105,246 B2 | 1/2012 | Voeller et al. |
| 8,118,862 B2 | 2/2012 | Saeed |
| 8,123,776 B2 | 2/2012 | Gilson et al. |
| 8,133,226 B2 | 3/2012 | Chou et al. |
| 8,146,400 B2 | 4/2012 | Goldfarb et al. |
| 8,172,862 B2 | 5/2012 | Wallace et al. |
| 8,197,424 B2 * | 6/2012 | Nabeshima ........... A61M 25/09 600/585 |
| 8,235,916 B2 | 8/2012 | Whiting et al. |
| 8,236,014 B2 | 8/2012 | Brenneman et al. |
| 8,241,311 B2 | 8/2012 | Ward et al. |
| 8,262,589 B2 | 9/2012 | Lupton |
| 8,267,882 B2 | 9/2012 | Euteneuer et al. |
| 8,292,908 B2 | 10/2012 | Nieman et al. |
| 8,308,658 B2 | 11/2012 | Albers et al. |
| 8,317,715 B2 | 11/2012 | Belleville et al. |
| 8,337,495 B1 | 12/2012 | Powlan |
| 8,377,084 B1 | 2/2013 | King, III et al. |
| 8,419,647 B2 | 4/2013 | Corl et al. |
| 8,419,648 B2 | 4/2013 | Corl et al. |
| 8,419,685 B2 | 4/2013 | Shivkumar et al. |
| 8,460,213 B2 | 6/2013 | Northrop |
| 8,460,214 B2 | 6/2013 | Kuban et al. |

(56) References Cited

U.S. PATENT DOCUMENTS

| | | | |
|---|---|---|---|
| 8,460,349 B2 | 6/2013 | Frenk et al. | |
| 8,470,025 B2 | 6/2013 | Lenihan et al. | |
| 8,485,969 B2 | 7/2013 | Grayzel et al. | |
| 8,500,656 B2 | 8/2013 | Lupton | |
| 8,540,676 B2 | 9/2013 | Geist et al. | |
| 8,551,020 B2 | 10/2013 | Chen et al. | |
| 8,551,133 B2 | 10/2013 | Watanabe et al. | |
| 8,579,832 B2 | 11/2013 | Von Malmborg et al. | |
| 8,579,912 B2 | 11/2013 | Isaza et al. | |
| 8,603,157 B2 | 12/2013 | Seguin et al. | |
| 8,613,712 B1 | 12/2013 | Burkett et al. | |
| 8,622,931 B2 * | 1/2014 | Teague | B29C 48/12 600/585 |
| 8,622,934 B2 | 1/2014 | Muzslay et al. | |
| 8,636,715 B2 | 1/2014 | Patel | |
| 8,641,747 B2 | 2/2014 | Brenneman et al. | |
| 8,668,657 B2 | 3/2014 | Solar et al. | |
| 8,679,035 B2 | 3/2014 | Boyle et al. | |
| 8,691,035 B2 | 4/2014 | Pingleton et al. | |
| 8,702,626 B1 | 4/2014 | Kim et al. | |
| 8,728,010 B2 | 5/2014 | Hirshman | |
| 8,852,125 B2 | 10/2014 | Von Malmborg | |
| 8,864,755 B2 | 10/2014 | Appling et al. | |
| 8,870,790 B2 | 10/2014 | Davis et al. | |
| 8,876,848 B2 | 11/2014 | Stien et al. | |
| 8,920,402 B2 | 12/2014 | Nash et al. | |
| 8,961,555 B2 | 2/2015 | Duerig et al. | |
| 9,028,427 B2 * | 5/2015 | Kinoshita | A61M 25/09 600/585 |
| 9,031,647 B2 | 5/2015 | Maskara et al. | |
| 9,044,201 B2 | 6/2015 | Samuelsson et al. | |
| 9,050,005 B2 | 6/2015 | Ignagni et al. | |
| 9,055,997 B2 | 6/2015 | Fifer et al. | |
| 9,095,465 B2 | 8/2015 | Kelly | |
| 9,095,685 B2 | 8/2015 | Sela et al. | |
| 9,149,604 B2 | 10/2015 | Nishide et al. | |
| 9,180,278 B2 * | 11/2015 | Kobayashi | A61L 29/085 |
| 9,206,575 B2 | 12/2015 | Miller et al. | |
| 9,855,408 B2 * | 1/2018 | Goldman | A61M 25/09 |
| 2002/0087100 A1 * | 7/2002 | Onuki | A61B 1/00098 600/585 |
| 2004/0039309 A1 * | 2/2004 | Murayama | A61M 25/09 600/585 |
| 2004/0167439 A1 | 8/2004 | Sharrow | |
| 2005/0075582 A1 | 4/2005 | Cornelius et al. | |
| 2005/0096665 A1 * | 5/2005 | Reynolds | A61M 25/09 606/108 |
| 2007/0118053 A1 * | 5/2007 | Melsheimer | A61B 90/94 600/585 |
| 2007/0255217 A1 * | 11/2007 | Burkett | B29C 48/05 604/164.13 |
| 2008/0171952 A1 | 7/2008 | Mishima | |
| 2008/0194991 A1 * | 8/2008 | Teague | B29C 48/155 600/585 |
| 2008/0228109 A1 * | 9/2008 | Kinoshita | A61M 25/09 600/585 |
| 2011/0172604 A1 * | 7/2011 | Wolfe | A61M 25/09 604/164.13 |
| 2015/0074995 A1 | 3/2015 | Patil et al. | |

* cited by examiner

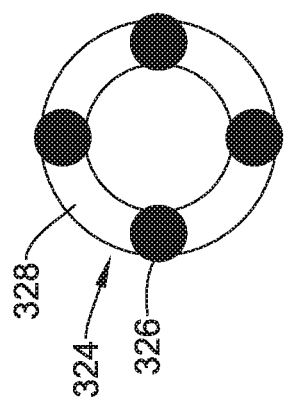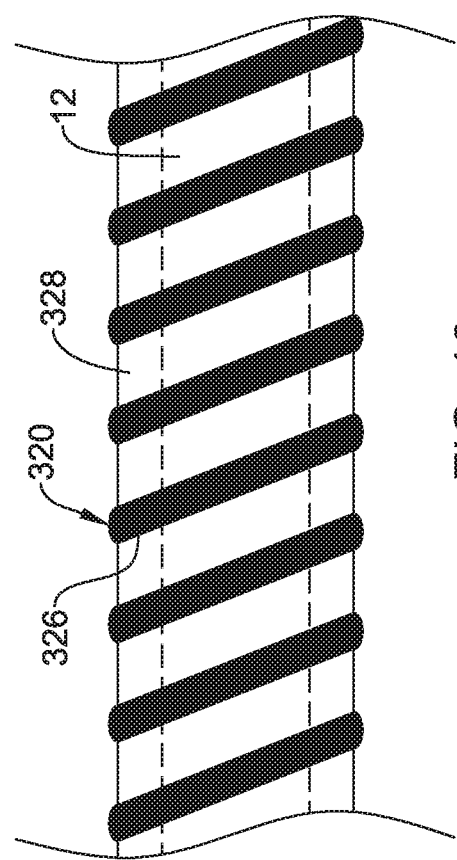

GUIDEWIRE WITH TACTILE FEEL

CROSS-REFERENCE TO RELATED APPLICATIONS

This application claims priority under 35 U.S.C. § 119 to U.S. Provisional Application Ser. No. 62/443,882, filed Jan. 9, 2017, the entirety of which is incorporated herein by reference.

TECHNICAL FIELD

The present disclosure pertains to medical devices, and methods for manufacturing medical devices. More particularly, the present disclosure pertains to guidewire with tactile feel.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An example guidewire is disclosed. The guidewire comprises: a core wire having a body region and a distal tip region; a distal tip member disposed along the distal tip region, the distal tip member having a proximal end; a sleeve disposed along the body region, the sleeve being disposed adjacent to the proximal end of the distal tip member and extending proximally therefrom; wherein the sleeve includes a first member and a heat shrink member; and wherein the first member has an uneven outer surface.

Alternatively or additionally to any of the embodiments above, the core wire includes a nickel-titanium alloy.

Alternatively or additionally to any of the embodiments above, the core wire includes stainless steel.

Alternatively or additionally to any of the embodiments above, the first member includes a braid.

Alternatively or additionally to any of the embodiments above, the first member includes a coil.

Alternatively or additionally to any of the embodiments above, the first member includes a helically-oriented region.

Alternatively or additionally to any of the embodiments above, the sleeve is designed to have a substantially constant outer surface prior to manufacturing the guidewire.

Alternatively or additionally to any of the embodiments above, the heat shrink member is designed to shrink during manufacturing of the guidewire such that the sleeve has an uneven outer surface after manufacturing the guidewire.

Alternatively or additionally to any of the embodiments above, the first member includes a polymer.

Alternatively or additionally to any of the embodiments above, the first member includes a metal.

Alternatively or additionally to any of the embodiments above, the first member is disposed radially inward of the heat shrink member.

An example method for manufacturing a guidewire is disclosed. The method comprises: disposing a distal tip member along a distal tip region of a core wire; disposing a sleeve along a body region of the core wire; wherein the sleeve includes a first member having an uneven outer surface and a heat shrink member; wherein the sleeve has a substantially constant outer surface; applying heat to the sleeve; and wherein applying heat the sleeve reduces the heat shrink member and alters the outer surface of the sleeve.

Alternatively or additionally to any of the embodiments above, the sleeve includes a co-extrusion of the first member and the heat shrink member.

Alternatively or additionally to any of the embodiments above, the first member includes a braid.

Alternatively or additionally to any of the embodiments above, the first member includes a coil.

Alternatively or additionally to any of the embodiments above, the first member includes a polymer.

An example method for manufacturing a guidewire is disclosed. The method comprises: disposing a distal tip member along a distal tip region of a core wire; disposing a composite sleeve along a body region of the core wire; wherein the composite sleeve includes a metallic inner member having an uneven outer surface and an outer heat shrink tube; wherein the composite sleeve has a substantially constant outer surface; applying heat to the composite sleeve; and wherein applying heat the composite sleeve reduces the heat shrink tube and alters the outer surface of the composite sleeve such that the uneven outer surface of the metallic inner member defines a textured surface along the guidewire.

Alternatively or additionally to any of the embodiments above, the composite sleeve includes a co-extrusion of the metallic inner member and the heat shrink tube.

Alternatively or additionally to any of the embodiments above, the metallic inner member includes a braid.

Alternatively or additionally to any of the embodiments above, the metallic inner member includes a coil.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIG. 9 is an end view of a portion of an example medical device.

FIG. 10 is a side view of a portion of an example medical device.

Figure 1:
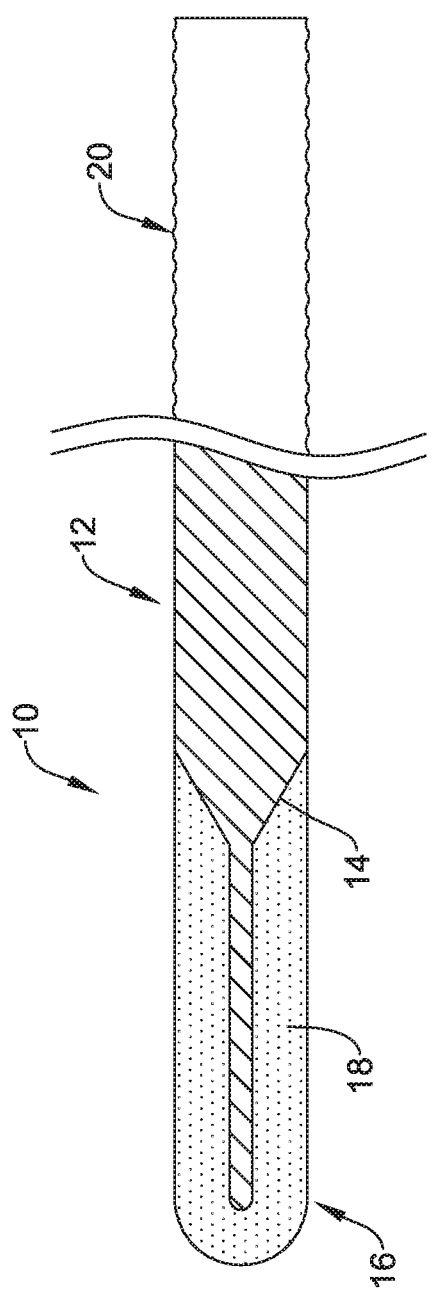
FIG. 1 is a partial cross-sectional side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

A number of medical procedures, including intravascular procedures, procedures along the digestive and/or biliary tract, ureteral procedures, etc. utilize medical devices such as guidewires. As less invasive procedures are devolved, there is an ongoing need for smaller devices. For example, in some current ureteral procedures, guidewires with an outer diameter of about 0.035-0.038 inches may be utilized. Even smaller guidewires may be desirable and when developing smaller guidewires, one goal may be to develop guidewires with the same features and characteristics of current "larger" guidewires. For example, it may be desirable for the smaller guidewires to have a desirable level of stiffness to allow for navigation and/or "pushability" of the guidewire through the anatomy.

One possible way to reduce the size of a guidewire is to remove components. For example, some urethral guidewires may have an outer coil wrapped around the outer surface of a core wire. While the outer coil may have a relatively small contribution to the stiffness of the guidewire, the coil may provide a clinician with a level of tactile feel such that the clinician can readily determine if and when the guidewire is moving while attempting to advance the guidewire. Removing this coil in order to reduce the size of the guidewire may result in a guidewire that still has a desirable level of stiffness. However, a "bare" core wire may lack the tactile characteristics that may be desirable to clinicians.

Disclosed herein are medical devices such as guidewires that are designed to have a number of desirable features. For example, the guidewires disclosed herein may have a desirable level of stiffness while being small enough to be suitable for less invasive procedures. In addition, the guidewires disclosed herein may include additional features that may add an improved tactile feel to "small" guidewires such that a clinician can readily use the guidewire in less invasive medical procedures.

FIG. 1 is a partial cross-sectional side view of an example medical device 10. In this example, the medical device 10 takes the form of a guidewire. However, in other instances, the medical device 10 can be a catheter, introducer, trocar, or the like. The guidewire 10 may include a core wire 12. In at least some instances, the core wire 12 is formed from a material that can provide the guidewire 10 with desirable flexibility/stiffness characteristics. For example, the core wire 12 may be formed from a metal, metal alloy, or polymer such as those disclosed herein. Some examples may include stainless steel and/or nickel-titanium alloys. The core wire 12 may be a single monolith of material or may include two or more segments secured together.

The core wire 12 may include a tapered region 14. In general, the tapered region 14 may be positioned adjacent to the distal end region of the core wire 12. This may provide for desirable flexibility at the distal end. However, this is not intended to be limiting. In some instances, the core wire 12 may include a single taper along the tapered region 14. Alternatively, the tapered region 14 may include a plurality of tapers. In some of these and in other instances, the taper(s) may include linear tapers, curvilinear tapers, stepped tapers, or the like. In examples where a plurality of tapers are present, a constant outer diameter section or "non-tapered" region may be disposed between tapers. Alternatively, some or all of the tapers may be positioned directly adjacent one another.

Figure 2:
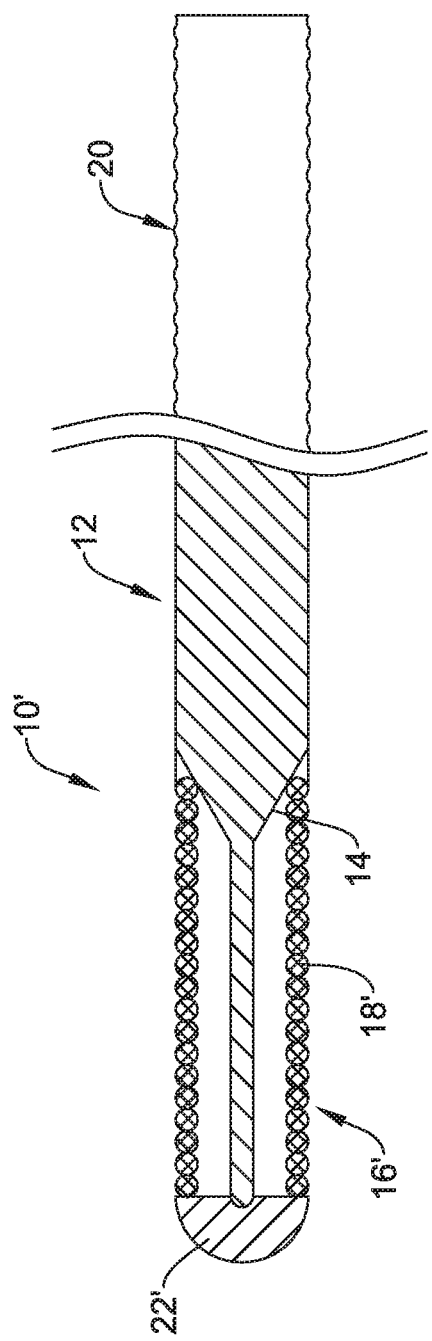
FIG. 2 is a partial cross-sectional side view of an example medical device.

A distal tip member 16 may be coupled to the core wire 12. The form of the distal tip member 16 may vary. For example, in the example shown in FIG. 1, the distal tip member 16 may include a polymeric sleeve or tip 18. In other words, the guidewire 10 may be considered to be a "poly tip" or "polymer tip" guidewire 10. Other forms of distal tips are contemplated. For example, FIG. 2 illustrates a medical device/guidewire 10' with a distal tip member 16' that includes a coil member 18'. In other words, the guidewire 10' may be considered to be a "spring tip" guidewire 10'. A tip 22', for example a solder ball tip, may be disposed at the distal end of the distal tip member 16'. These are just examples. Other distal tips are contemplated.

As indicated above, the core wire 12 may be designed to provide the guidewire 10 (and/or the guidewire 10') with a desirable level of flexibility/stiffness. In addition, the guidewire 10 (and/or the guidewire 10') may include a textured region 20. The textured region 20 may be designed to provide the guidewire 10 (and/or the guidewire 10') with a desirable level of tactile feel such that a clinician may be able to "feel" the guidewire 10 during use and/or navigation thereof. The textured region 20 is designed to have a minimal impact on the outer diameter of the guidewire 10. In other words, the textured region 20 is designed to be relatively thin such that the guidewire 10 (and/or the guidewire 10') can be manufactured to have a relatively small outer diameter and be suitable for less invasive medical procedures. For example, the guidewire 10 (and/or the guidewire 10') can have an outer diameter of about 0.038 inches or less, an outer diameter of about 0.035 inches or less, an outer diameter of about 0.01 to 0.035 inches, or an outer diameter of about 0.014-0.035 inches.

Figure 3:
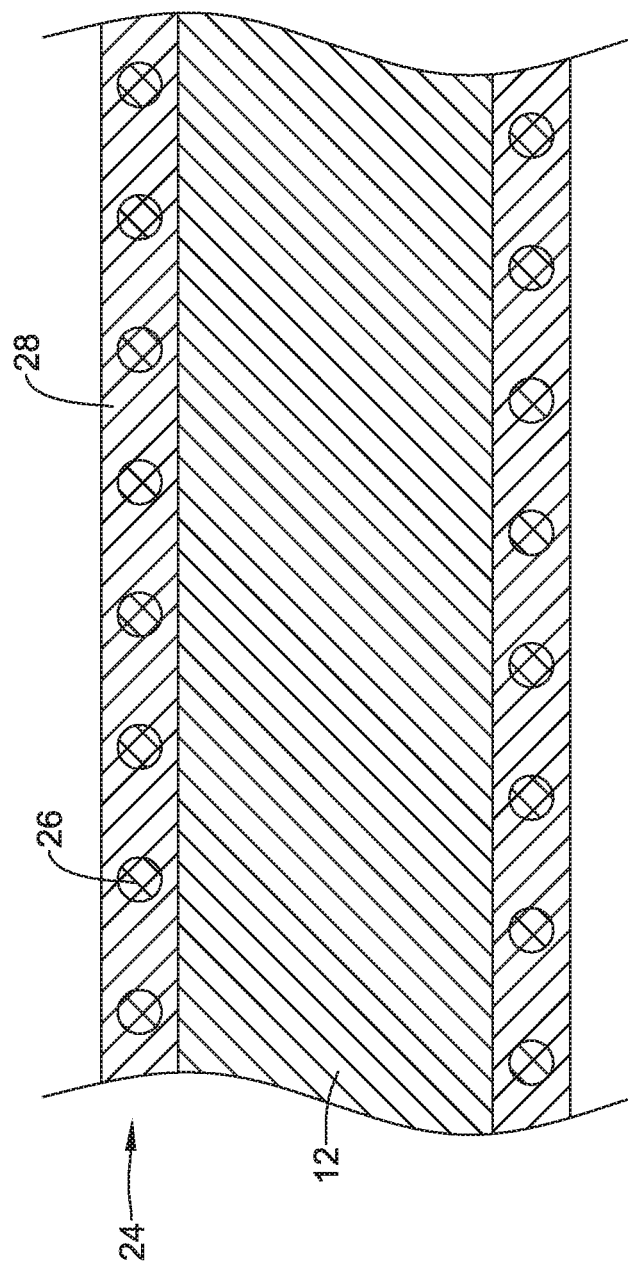
FIG. 3 is a cross-sectional view of a portion of an example medical device.

Adding the textured region 20 to the guidewire 10 (and/or the guidewire 10') may include disposing a sleeve 24 along the core wire 12 as shown in FIG. 3. When doing so, the sleeve 24 may be disposed along a proximal region of the core wire 12. This may include disposing the sleeve 24 along the core wire 12 from at or near the distal tip member 16 to the proximal end of the core wire 12. For example, the core wire may include a body region and a distal tip region (e.g., at or adjacent to the distal tip member 16), and the sleeve 24 may be disposed along the body region. This may include disposing the sleeve 24 at or adjacent to the proximal end of the distal tip member 16 and proximally therefrom along the body region. Other configurations are contemplated. In some instances, a plurality of sleeves 24 may be used to form a plurality of textured regions 20 along the core wire 12.

The sleeve 24 may include a first member 26 and a second member 28. The sleeve 24 may be formed by a suitable process such as extrusion (e.g., co-extrusion). When doing so, the first member 26 may be embedded within the second member 28. In at least some of these instances, the sleeve 24 may have a constant outer diameter, a constant inner diameter, or both. For example, the sleeve may take the form of a cylindrical tube. In addition, in at least some instances, a least a portion of the first member 26 is positioned radially inward of the outer surface of the sleeve 24 (and/or a least a portion of the first member 26 is positioned radially inward of the outer surface of the second member 28).

In at least some instances, the first member 26 includes a structure or structural feature that has an uneven outer surface. For example, the first member 26 may include a braid, coil, member having a helically-oriented region, mesh, or the like. The first member 26 may be formed from a metal, metal alloy, polymer, combinations thereof, or the like including those material disclosed herein. In at least some instances, the first member 26 includes a material or structure that does not change dimensionally when heat is applied. In other words, the first member 26 may not be considered to be a "heat shrink material". Conversely, the second member 28 may be formed from a heat shrinkable material. In at least some of these instances, the application of heat to the sleeve 24 may cause the second member 28 to shrink. When doing so, the second member 28 may shrink onto the first member 26, fill any gaps or voids between the uneven surface characterizes of the first member 26, and/or otherwise allow the uneven surface characteristics of the first member 26 to become visible, exposed, and/or prominent along the core wire 12. This provides a clinical with a desirable level of tactile feel such that the guidewire 10 (and/or the guidewire 10') can be easily navigated through the anatomy.

Figure 4:
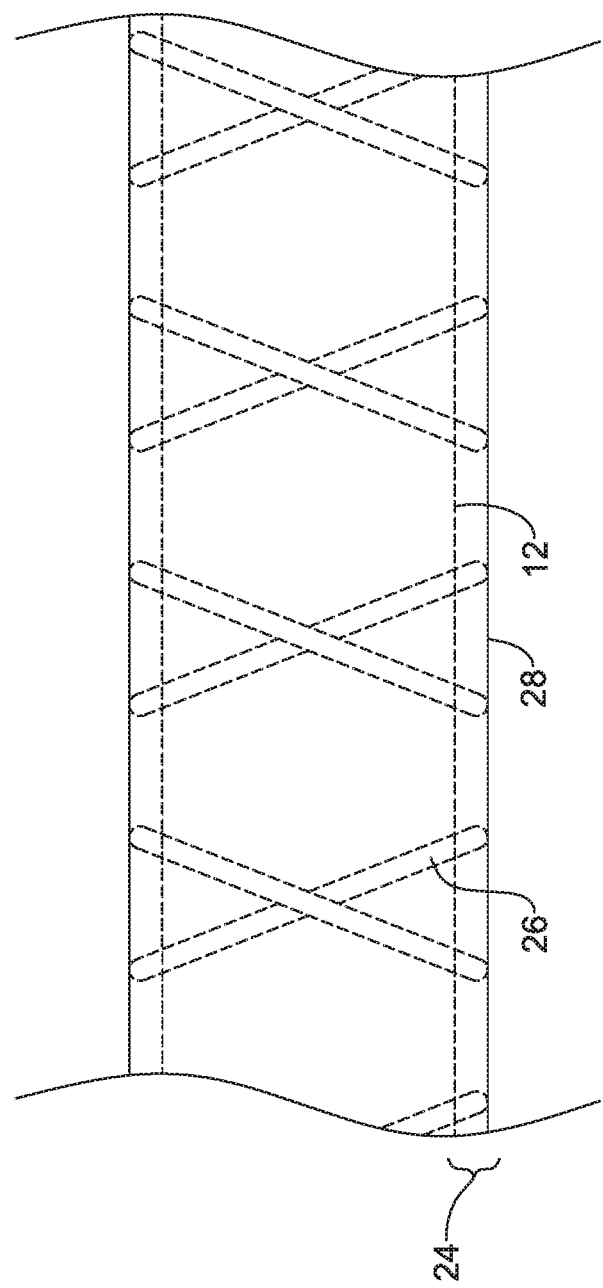
FIG. 4 is a partial cross-sectional view of a portion of an example medical device.
Figure 5:
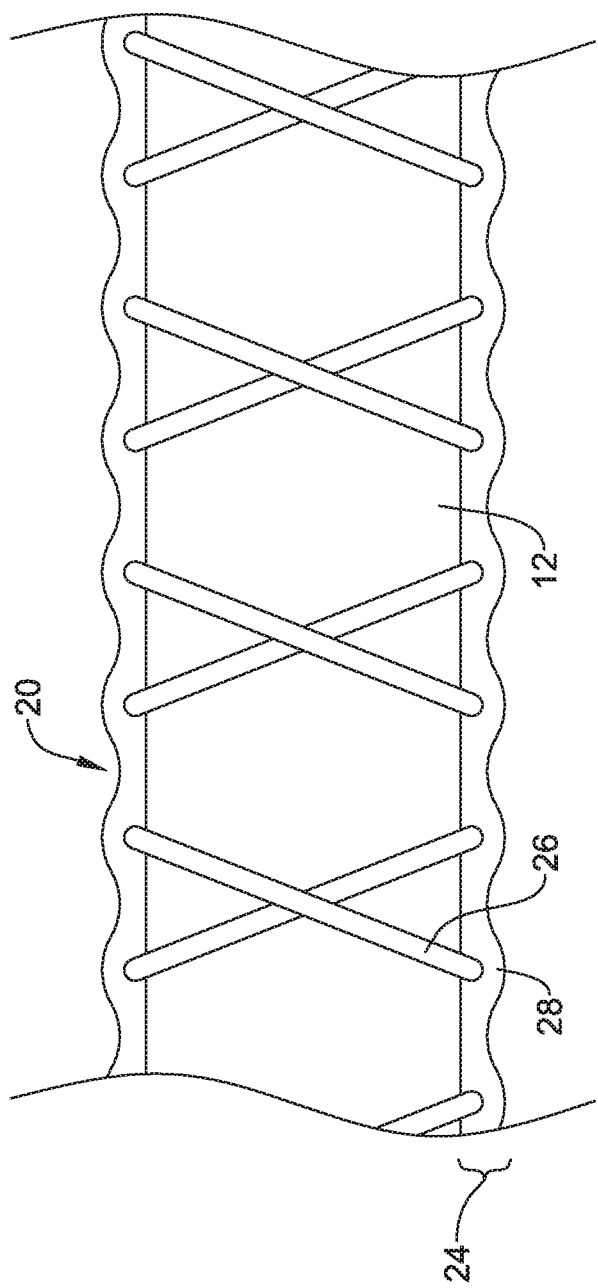
FIG. 5 is a partial cross-sectional view of a portion of an example medical device.

FIG. 4 illustrates the sleeve 24 disposed along the core wire 12. In this example, the first member 26 may take the form of a braid. Prior to the application of heat, the sleeve 24 may have a constant outer diameter. After application of heat, the second member 28 may shrink onto the first member 26 as shown in FIG. 5 to define the textured region 20. When doing so, the second member 28 may at least partially fill or otherwise be disposed along any spaces or voids present in the first member 26.

Figure 6:
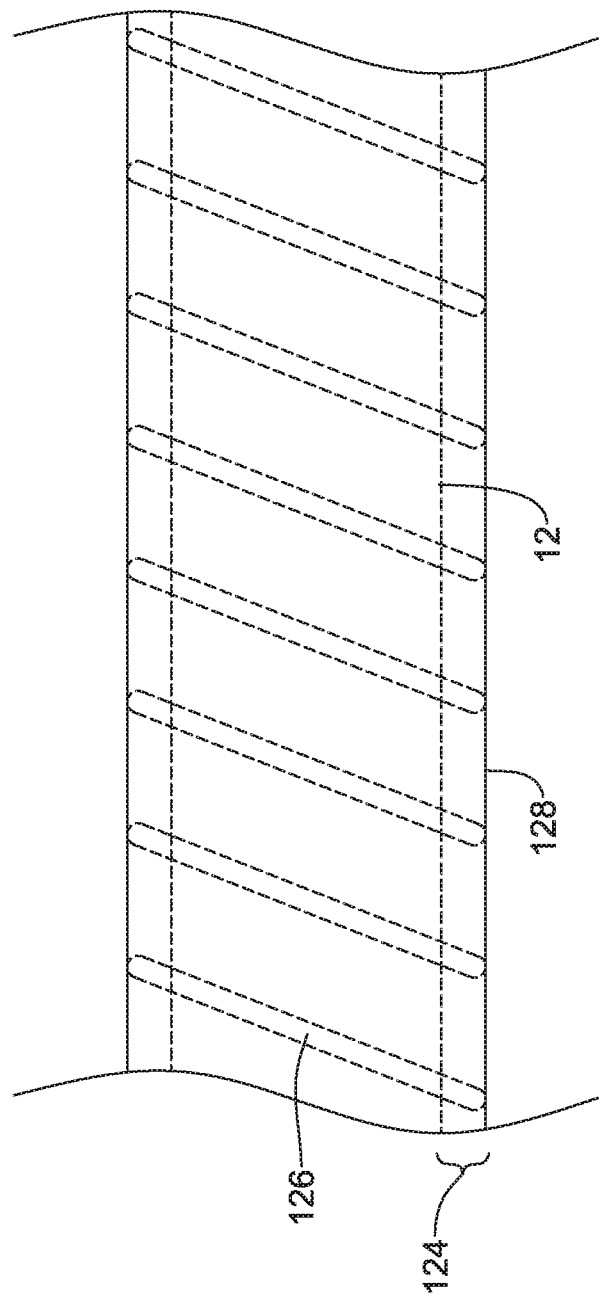
FIG. 6 is a partial cross-sectional view of a portion of an example medical device.
Figure 7:
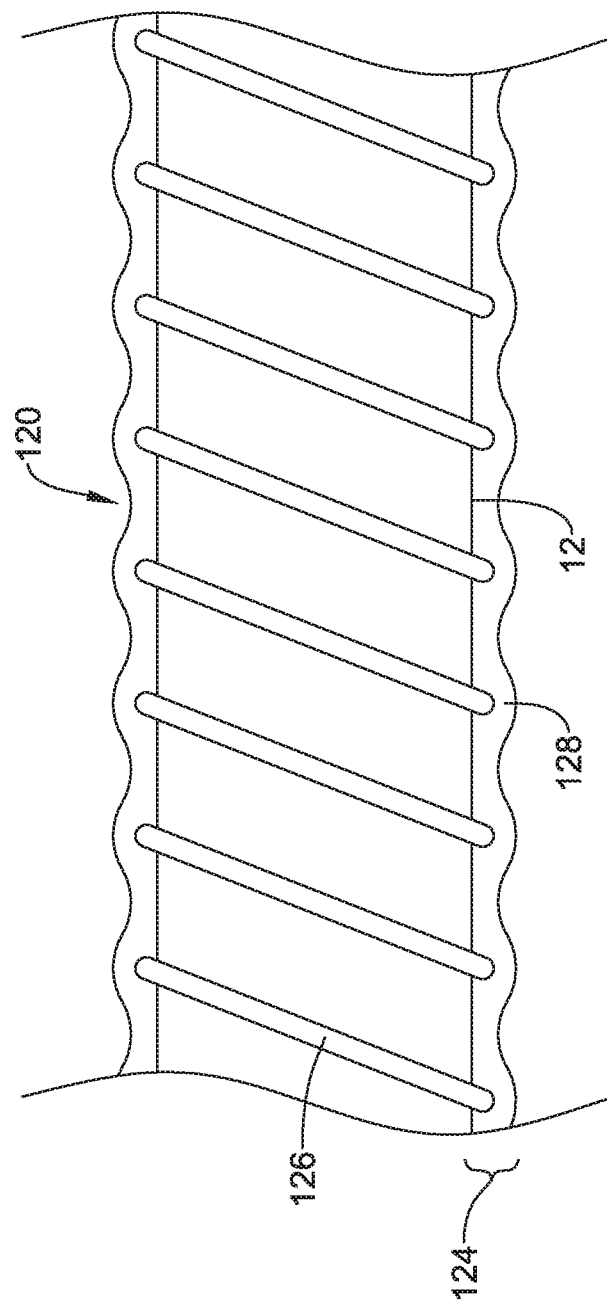
FIG. 7 is a partial cross-sectional view of a portion of an example medical device.

The form of the sleeve 24 (and/or the first member 26, the second member 28, or both) may vary. For example, FIG. 6 illustrates another example sleeve 124 disposed along the core wire 12. In this example, the first member 126 may take the form of a coil. Prior to the application of heat, the sleeve 124 may have a constant outer diameter. After application of heat, the second member 128 may shrink onto the first member 126 as shown in FIG. 7 to define the textured region 120. When doing so, the second member 128 may at least partially fill or otherwise be disposed along any spaces or voids present in the first member 126.

Figure 8:
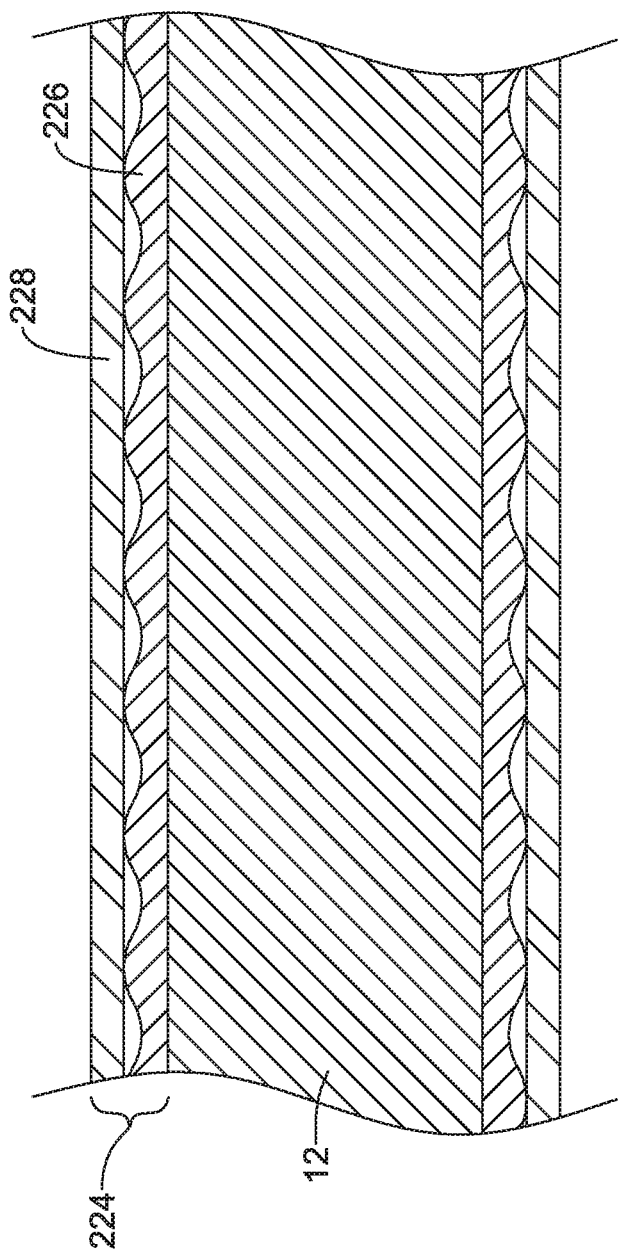
FIG. 8 is a cross-sectional view of a portion of an example medical device.

As indicated above, the sleeve 24/124 may take the form of an extruded/co-extruded, cylindrical tube that includes the first member 26/126 and the second member 28/128. A number of additional sleeves are contemplated. For example, FIG. 8 is a cross-sectional view of another example sleeve 224 disposed along the core wire 12. The sleeve 224 may include a first member 226 and a second member 228. In this example, the first member 226 may take the form of a first layer of material and the second member 228 may take the form of a second layer of material. In other words, the first member 226 and the second member 228 may be two distinct layers that are secured together. In at least some instances, the first member 226 may take the form of a braid, coil, member having a helically-oriented region, mesh, or the like. The braid, coil, member having a helically-oriented region, mesh, or the like may be a single structure or layer or may include a coating or covering. The second member 228 may take the form of a generally cylindrical sleeve. In at least some instances, a space or gap may be formed between the first member 226 and the second member 228. Alternatively, the inner surface of the second member 228 may conform to the outer surface of the first member 226. Application of heat to the sleeve 224 may result in shrinking of the second member 228 such that the uneven outer surface of the first member 226 to become visible, exposed, and/or prominent along the core wire 12 in a manner similar to what is disclosed herein.

FIG. 9 is an end view of another example sleeve 324 that may be similar in form and function to other sleeves disclosed herein. The sleeve 324 may include a plurality of first members 326 and a second member 328. The first members 326 may form a plurality of raised "stripes" along the sleeve 324. In some instances, the sleeve 324 may be extruded in a first or "striped" configuration where the first members 326 extend axially along the sleeve 324. The sleeve 324 can be twisted or otherwise exposed to torque to shift the sleeve 324 to a second configuration where the first members 326 are helically oriented as shown in FIG. 10. The sleeve 324, whether in the first configuration or the second configuration can be coupled to the core wire 12 and define a textured region 320. In some instances, the sleeve 324 can be formed from heat shrink material(s) and can be secured to the core wire 12 by heating. In some of these and in other instances, the sleeve 324 can positioned along the core wire 12 and heated to reflow the sleeve 324 and secure the sleeve 324 to the core wire 12. In some of these and in other instances, the sleeve 324 may be adhesively bonded to the core wire 12 (e.g., the sleeve 324 may include a layer of adhesive along an inner surface thereof).

The materials that can be used for the various components of medical device 10 (and/or other guidewires disclosed herein) and the various tubular members disclosed herein may include those commonly associated with medical devices. For simplicity purposes, the following discussion makes reference to core wire 12 and other components of medical device 10. However, this is not intended to limit the devices and methods described herein, as the discussion may be applied to other similar tubular members and/or components of tubular members or devices disclosed herein.

Core wire 12 and/or other components of medical device 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP).

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of medical device 10 to achieve the same result.

In some embodiments, a degree of Magnetic Resonance Imaging (MRI) compatibility is imparted into medical device 10. For example, medical device 10, or portions thereof, may be made of a material that does not substantially distort the image and create substantial artifacts (e.g., gaps in the image). Certain ferromagnetic materials, for example, may not be suitable because they may create artifacts in an MRI image. Medical device 10, or portions thereof, may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A guidewire, comprising:
a core wire having a body region and a distal tip region;
wherein the body region has a substantially constant outer diameter;
wherein the distal tip region includes one or more tapered sections;
a distal tip member disposed along the distal tip region, the distal tip member having a proximal end;
a sleeve having a proximal end defining a proximal end of the guidewire, the sleeve extending along the body region to a position adjacent to the proximal end of the distal tip member;
wherein the sleeve includes a first member and a heat shrink member;
wherein the first member is disposed radially inward of the heat shrink member; and
wherein a first section of the sleeve extending distally from the proximal end of the sleeve has an uneven outer surface.

2. The guidewire of claim 1, wherein the core wire includes a nickel-titanium alloy.

3. The guidewire of claim 1, wherein the core wire includes stainless steel.

4. The guidewire of claim 1, wherein the first member includes a braid.

5. The guidewire of claim 1, wherein the first member includes a coil.

6. The guidewire of claim 1, wherein the first member includes a helically-oriented region.

7. The guidewire of claim 1, wherein the sleeve is designed to have a substantially constant outer surface prior to manufacturing the guidewire.

8. The guidewire of claim 7, wherein the heat shrink member is designed to shrink during manufacturing of the guidewire such that the sleeve has the uneven outer surface after manufacturing the guidewire.

9. The guidewire of claim 1, wherein the first member includes a polymer.

10. The guidewire of claim 1, wherein the first member includes a metal.

11. The guidewire of claim 1, wherein the sleeve has a second section extending between the first section and the distal tip member.

12. The guidewire of claim 11, wherein the second section of the sleeve has an even outer surface.

13. A guidewire, comprising:
- a core wire having a proximal end, a body region, and a distal tip region;
- wherein the body region has a substantially constant outer diameter;
- wherein the distal tip region includes one or more tapered sections;
- a distal tip member disposed along the distal tip region, the distal tip member having a proximal end; and
- a sleeve extending along the body region, the sleeve having a textured region extending distally from the proximal end of the core wire and a smooth region extending between the textured region and the distal tip region; and
- wherein the textured region includes heat shrink member and a first member that is disposed radially inward of the heat shrink member.

* * * * *